US00PP08945P

United States Patent [19]

Oelsen et al.

[11] Patent Number: Plant 8,945

[45] Date of Patent: Oct. 18, 1994

[54] MINIATURE ROSE PLANT NAMED POULTVER

[75] Inventors: Mogens N. Oelsen; Pernille Olesen, both of Fredensborg, Denmark

[73] Assignee: Bear Creek Gardens, Inc., Medford, Oreg.

[21] Appl. No.: 150,466

[22] Filed: Nov. 9, 1993

[51] Int. Cl.[5] ..... A01H 5/00

[52] U.S. Cl. ..... Plt./9

[58] Field of Search ..... Plt. 9, 10, 7.1

*Primary Examiner*—Howard J. Locker

*Attorney, Agent, or Firm*—Klarquist Sparkman Campbell Leigh & Whinston

[57] ABSTRACT

Miniature rose plant having a long shelf life, attractive and unique flower color, ease of propagation by softwood cuttings, and a vigorous and compact habit of growth.

1 Drawing Sheet

The present invention relates to a new and distinct variety of rose plant of the miniature class which was originated by us by crossing two unnamed seedlings.

The primary objective of this breeding was to produce a new pot rose variety with a good keeping quality, especially for production in 6 to 8 cm pots. The objective was substantially achieved, along with other desirable improvements, as evidenced by the following unique combination of characteristics that are outstanding in the new variety and that distinguish it from its parents, as well as from all other varieties of which we are aware:

1. Attractive, unique flower color (Red Group 52C);
2. Vigorous compact habit of growth;
3. Ease of propagation from softwood cutting; and
4. Long pot rose shelf life.

Asexual reproduction of this new variety by budding and softwood cuttings, as performed at Fredensborg, Denmark, and Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed decription of our new rose cultivar with color descriptions using terminology in accordance with The Royal Horticultural Society (London) Colour Chart, except where ordinary dictionary significance of color is indicated.

Parentage:

*Seed parent.*—Unnamed seedling.

*Pollen parent.*—Unnamed seedling.

Classification:

*Botanical.*—*Rosa hybrida.*

*Commercial.*—Miniature.

FLOWER

Observations made from specimens grown in a garden environment at Fredensborg, Denmark, in 1991.

Blooming habit: Continuous.

Bud:

*Size.*—1.5 cm long when the petals start to unfurl.

*Form.*—Pointed ovoid to globular.

*Color.*—When sepals first divide, bud color is Red Group 52D. When half blown, the upper sides of the petals are Red Group 52D; and the lower sides of the petals are Red Group 52C.

*Sepals.*—Color: Green Group 138B. Surface texture: Covered in fine hairs. There are three lightly appendaged sepals. There are two unappendaged sepals with hairy edges.

*Receptacle.*—Color: Green Group 138C. Shape: Pear. Size: Small (1 cm×1 cm). Surface: Smooth.

*Peduncle.*—Length: Short (3.8 cm to 4.5 cm). Surface: Smooth. Color: Green Group 137D. Strength: Stiff, erect.

Bloom:

*Size.*—Small. Average open size is 3.5 cm in diameter.

*Borne.*—Several together, in pyramidal clusters of 3 to 5 flowers.

*Stems.*—Medium to short (15.2 cm to 17.8 cm), strong.

*Form.*—When first open: Globular. Permanence: Flattens, all petals curl.

*Petalage.*—Number of petals under normal conditions: 20 to 40.

*Color.*—The upper side of the petals is Red Group 52D. The reverse side of the petals is Red Group 52C. The base of each petal is Yellow Group 4D at the point of attachment. The major color on the upper side is Red Group 52D.

Variegations.—None.

*Discoloration.*—The general tonality at the end of the first day: No change. At the end of the third day, no change. By the 8th day there is a lightening of intensity to Red Group 55C.

*Fragrance.*—Slight.

Petals:

*Texture.*—Thin.

*Shape.*—Pointed oval.

*Form.*—Tips slightly recurved; moderately quilled.

*Arrangement.*—Imbricated, with many small petaloids in the center.

*Persistence.*—Drop off cleanly.

*Lastingness.*—On the plant: Very long (14 to 18 days). As a cut flower: Very long (10 to 12 days).

Reproductive parts:

*Anthers.*—Size: Small. Quantity: Many. Color: Yellow. Arrangement: Regular around the styles.

*Filaments.*—Color: White.
*Pollen.*—Color: Gold Yellow.
*Styles.*—Color: Greenish white.
*Stigmas.*—Color: Greenish white.

Form: Bush.

Growth: Vigorous, dwarf, compact.

Foliage:

*Number of leaflets on the normal mid-stem leaves.*—5.
*Size.*—Small (length 5 to 6 cm; width is 3 to 4 cm).
*Quantity.*—Normal.
*Color.*—New foliage: Green Group 137C. Old foliage: Green Group 139A.

Leaflets:

*Shape.*—Broadly oval.
*Texture.*—Upper side: Smooth.
*Edge.*—Serrated.
*Serration.*—Single, small.
*Petiole rachis.*—Color: Green.
*Petiole underside.*—Smooth with occasional prickles.
*Stipules.*—Medium, serrated.

*Disease resistance.*—Resistant to mildew and blackspot under normal growing conditions in a garden environment in Fredensborg, Denmark.

Wood:

*New wood.*—Color: Light green. Bark: Smooth.
*Old wood.*—Color: Green. Bark: Smooth.

Prickles:

*Quantity.*—On main canes from base: Ordinary. On laterals from main canes: Few.
*Form.*—Short (0.3 cm long), straight.
*Color when young.*—Translucent.

Small prickles:

*Quantity.*—Few on main stalks and on laterals.
*Color.*—Green.

We claim:

1. A new and distinct variety of rose plant of the miniature class, substantially as herein shown and described, characterized particularly as to novelty by the unique combination of a long shelf life, attractive and unique flower color, ease of propagation by softwood cuttings, and a vigorous and compact habit of growth.

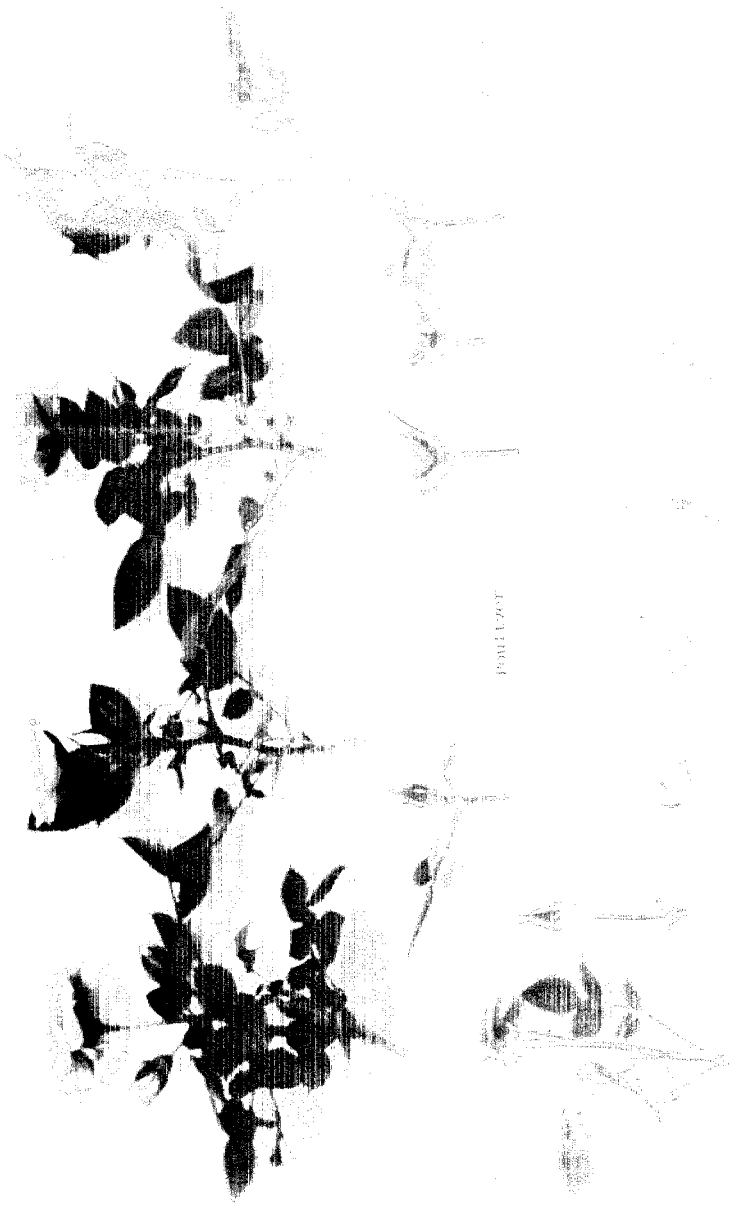

* * * * *